United States Patent [19]

Grosscurt et al.

[11] Patent Number: 5,164,396

[45] Date of Patent: Nov. 17, 1992

[54] BARBITURIC ACID DERIVATIVES HAVING INSECTICIDAL ACTIVITY

[75] Inventors: Arnoldus C. Grosscurt; Jan W. Terpstra, both of Weesp, Netherlands

[73] Assignee: Duphar International Research B.V., Weesp, Netherlands

[21] Appl. No.: 693,863

[22] Filed: May 1, 1991

[30] Foreign Application Priority Data

May 4, 1990 [NL] Netherlands ............... 9001075

[51] Int. Cl.$^5$ ............... A61K 31/515; C07D 239/02
[52] U.S. Cl. ............... 514/270; 544/299; 544/302
[58] Field of Search ............... 544/299, 302; 514/270

[56] References Cited

U.S. PATENT DOCUMENTS

| | | | |
|---|---|---|---|
| 3,322,526 | 5/1967 | Loux | 544/299 |
| 3,828,043 | 8/1974 | Kay et al. | 544/302 |
| 3,999,974 | 12/1976 | Hirino et al. | 71/92 |
| 4,244,939 | 1/1981 | Parsons, Jr. et al. | 544/299 |
| 4,748,178 | 5/1988 | Burckhardt et al. | 514/270 |

FOREIGN PATENT DOCUMENTS 2524578 12/1975 Fed. Rep. of Germany .

OTHER PUBLICATIONS

Moelants et al, CA 86-56768z (1976).
Hirono et al. CA 84-121891j (1976).

*Primary Examiner*—Cecilia Tsang
*Attorney, Agent, or Firm*—Stevens, Davis, Miller & Mosher

[57] ABSTRACT

The invention relates to new barbituric acid derivatives of the general formula

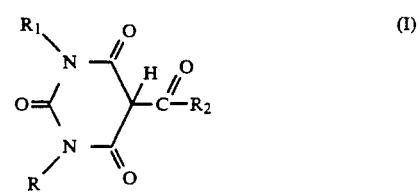

wherein
R is a substituted or unsubstituted phenyl group or heteroaryl group having 5 or 6 ring atoms, the heteroaryl group comprising one or more hetero atoms selected from the group consisting of N, O and S, and the substituents being selected from the group consisting of halogen, cyano, nitro, formyl, acetyl, $C_1$–$C_4$ alkyl, $C_1$–$C_4$ haloalkyl, $C_1$–$C_4$ alkoxy, $C_1$–$C_4$ haloalkoxy and optionally substituted phenoxy;
$R_1$ is a $C_3$–$C_5$ alkyl group, a $C_3$–$C_5$ alkenyl group, a $C_3$–$C_5$ alkynyl group, a cyclopropyl group or a cyclopropyl($C_1$–$C_4$)alkyl group, and
$R_2$ is a $C_1$–$C_4$ alkyl group or an amino group;

as well as salts and metal complexes of the said compounds.

These compounds may be used in compositions for the control of insects, in particular aphids, in agriculture, horticulture and silviculture.

11 Claims, No Drawings

BARBITURIC ACID DERIVATIVES HAVING INSECTICIDAL ACTIVITY

The invention relates to new barbituric acid derivatives and to a method of preparing the new compounds. The invention also relates to insecticidal compositions based on the said compositions and to the use of the said compounds for controlling insects, in particular aphids, in agriculture, horticulture and silviculture.

Netherlands Patent application 7109160 describes barbituric acid derivatives an 2-thiobarbituric acid derivatives having a pesticidal activity, for example, against insects such as aphids. Examples of compounds disclosed in the said Patent application are 1,3-dimethyl-5-acetyl-2-thiobarbituric acid, 1,3-dimethyl-5-benzoyl-2-thiobarbituric acid, 1,3-dimethyl-5-cyclohexylcarbonyl-2-thiobarbituric acid and 1-methyl-3-n-propyl-5-acetylbarbituric acid. As will become apparent from the specific examples, the said compounds, however, prove to be inactive or not sufficiently active in quantities which are acceptable for practical applications.

It is the object of the invention to provide new barbituric acid derivatives having an improved aphicidal activity. This object can be achieved by means of barbituric acid derivatives which are characterized according to the present invention by the general formula

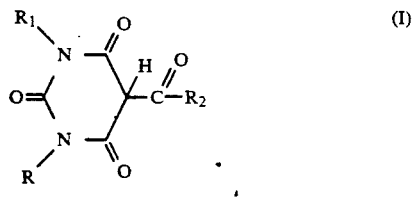

wherein
R is a substituted or unsubstituted phenyl group or heteroaryl group having 5 or 6 ring atoms, the heteroaryl group comprising one or more hetero atoms selected from the group consisting of N, O and S, and the substituents being selected from thegroup consisting of halogen, cyano, nitro, formyl, acetyl, $C_1-C_4$ alkyl, $C_1-C_4$ haloalkyl, $C_1-C_4$ alkoxy, $C_1-C_4$ haloalkoxy and optionally substituted phenoxy;
$R_1$ is a $C_3-C_5$ alkyl group, a $C_3-C_5$ alkenyl group, a $C_3-C_5$ alkenyl group, a cyclopropyl group or a cyclopropyl($C_1-C_4$)alkyl group; and
$R_2$ is a $C_1-C_4$ alkyl group or an amino group;
and by means of salts and metal complexes of the said compounds.

Examples of suitable heteroaryl groups are thienyl, pyridyl, thiazolyl, oxazolyl, pyrrolyl, triazolyl, oxadiazolyl, thiadiazolyl and pyrimidinyl. Examples of suitable salts are alkali metal salts such as sodium barbiturates and potassium barbiturates, and tetralalkyl ammonium salts. Examples of suitable metal complexes are complexes with ions of metals such as nickel, copper or zinc.

Due to a strong aphicidal activity compounds are preferred of the general formula

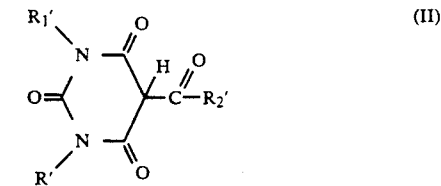

wherein
R' is an unsubstituted phenyl group or a phenyl group which is substituted with 1 or 2 substituents selected from the group consisting of halogen, nitro, cyano and $C_1-C_4$ alkyl,
$R'_1$ is an allyl group, a methylallyl group, a propargyl group, a cyclopropyl group or a cyclopropylmethyl group,
$R'_2$ is a methyl group or ethyl group;
as well as salts and metal complexes of the said compounds.

Examples of very suitable compounds according to the invention are:
(1) 1-phenyl-3-methylallyl-5-acetylbarbituric acid,
(2) 1-phenyl-3-allyl-5-acetylbarbituric acid,
(3) 1-phenyl-3-propargyl-5-acetylbarbituric acid,
(4) 1-(3-chlorophenyl)-3-allyl-5-acetylbarbituric acid,
(5) 1-phenyl-3-cyclopropylmethyl-5-acetylbarbituric acid,
(6) 1-(4-fluorophenyl)-3-methylallyl-5-acetylbarbituric acid,
(7) 1-(3-cyanophenyl)-3-methylallyl-5-acetylbarbituric acid,
(8) sodium 1-phenyl-3-propargyl-5-acetylbarbiturate,
(9) 1-(3-cyanophenyl)-3-allyl-5-acetylbarbituric acid,
(10) 1-(3-cyanophenyl)-3-propargyl-5-acetylbarbituric acid,
(11) 1-(3-fluorophenyl)-3-methylallyl-5-acetylbarbituric acid,
(12) 1-(3-methylphenyl)-3-methylallyl-5-acetylbarbituric acid,
(13) 1-(3-cyanophenyl)-3-cyclopropylmethyl-5-acetylbarbituric acid, and
(14) 1-(2-cyanophenyl)-3-methylallyl-5-acetylbarbituric acid; as well as the alkali metal salts of compounds (1) to (7) and (9) to 14.

Examples of other barbituric acid derivatives having insectidal activity according to the invention are:
(15) 1-phenyl-3-n-butyl-5-acetylbarbituric acid,
(16) 1-phenyl-3-isobutyl-5-acetylbarbituric acid,
(17) 1-(4-chlorophenyl)-3-allyl-5-acetylbarbituric acid,
(18) sodium 1-(3-chlorophenyl)-3-methylallyl-5-acetyl barbiturate,
(19) 1-(3-cyanophenyl)-3-isobutyl-5-acetylbarbituric acid,
(20) 1-(3-bromophenyl)-3-methylallyl-5-acetylbarbituric acid,
(21) 1-phenyl-3-cyclopropyl-5-acetylbarbituric acid,
(22) 1-phenyl-3-cyclopropylmethyl-5-carbamoylbarbituric acid,
(23) 1-(3-nitrophenyl)-3-cyclopropylmethyl-5-acetylbarbituric acid,
(24) 1-(3-cyanophenyl)-3-cyclopropyl-5-acetylbarbituric acid,
(25) 1-(3-cyano-4-fluorophenyl)-3-methylallyl-5-barbituric acid,
(26) 1-(3-trifluoromethoxyphenyl)-3-methylallyl-5-acetylbarbituric acid,

(27) 1-(3-cyano-4-fluorophenyl)-3-cyclopropylmethyl-5-acetyl barbituric acid,
(28) 1-phenyl-3-t.butyl-5-acetylbarbituric acid,
(29) 1-phenyl-3-methylallyl-5-propionylbarbituric acid,
(30) 1-(3,5-dichlorophenyl)-3-cyclopropylmethyl-5-acetylbarbituric acid,
(31) 1-(3-trifluoromethoxyphenyl)-3-cyclopropylmethyl-5-acetylbarbituric acid,
(32) 1-(3,5-dichlorophenyl)-3-cyclopropyl-5-acetylbarbituric acid,
(33) 1-(3-methylphenyl)-3-cyclopropylmethyl-5-acetylbarbituric acid,
(34) 1-(3-methylthiophenyl)-3-methylallyl-5-acetylbarbituric acid,
(35) 1-(3-trifluoromethylphenyl)-3-cyclopropylmethyl-5-acetylbarbituric acid,
(36) 1-(3-cyanophenyl)-3-isopropyl-5-acetylbarbituric acid,
(37) 1-(3,5-dichlorophenyl)-3-n-propyl-5-acetylbarbituric acid,
(38) 1-(3,5-dicyanophenyl)-3-cyclopropylmethyl-5-acetylbarbituric acid,
(39) 1-(2,6-dichloropyridyl-4)-3-cyclopropylmethyl-5-acetylbarbituric acid,
(40) 1-(3-iodophenyl)-3-cyclopropylmethyl-5-acetylbarbituric acid, and
(41) 1-(2,6-difluorophenyl)-3-cyclopropylmethyl-5-acetylbarbituric acid;
as well as the free acid of compound (18) and the alkali metal salts of compounds (15) to (17) and (19) to (41).

The substances according to the invention may be used for the control of various types of aphids in agriculture, horticulture and silviculture, for example, *Aphis fabae* (black beam aphid), *Acyrthosiphon pisum* (pea aphid), *Brevicoryne brassicae* (mealy cabbage aphid), *Sitobion avenae* (grain aphid), *Myzus persicae* (green peach aphid), *Aphis gossypii* (cotton aphid), *Macrosiphon euphorbiae* (potato aphid) and *Phopalosiphum padi* (oat-bird cherry aphid), as well as for the control of other insects, for example, beetles such as *Deptinotarsa decmlineata* (Colorado beetle).

For practical application the substances according to the invention are processed to compositions. In such compositions the active substance is mixed with solid carrier material or is dissolved or dispersed in liquid carrier material, if desired in combination with auxiliary substances, for example, emulsifiers, wetting agents, dispersing agents and stabilizers.

Examples of compositions according to the invention are aqueous solutions (SL) and dispersions (SC), oil dispersions, solutions in organic solvents (for example, DC), pastes, dusting powders (DP), dispersible powders (WP), wettable granules (WG), miscible oils (EC), granules, pellets, invert emulsions, aerosol compositions and fumigating agents.

Various of the above-mentioned compositions, for example, dispersible concentrates and powders, pastes and miscible oils, are in concentrate form and should be diluted prior to or during use.

The invert emulsions and solutions in organic solvents are mainly used in air application, namely when large areas are treated with a comparatively small quantity of composition. The invert emulsion may be prepared in the spraying apparatus shortly before or even during spraying by emulsifying water in an oil solution or an oil dispersion of the active substance.

The solutions of the active substance in organic solvents may be provided with a phytotoxicity-reducing substance, for example, wool fat, wool fatty acid or wool fatty alcohol.

A few examples of forms of composition will now be described in greater detail by way of example.

Granular compositions are prepared, for example, by taking up the active substance in a solvent or dispersing it in a diluent and impregnating the resulting solution/suspension, optionally in the presence of a binder, in granular carrier material, for example, porous granules (for example, pumice and attaclay), adding it to mineral non-porous granules (sand or ground marlow), or adding it to organic granules (for example, dried coffee-grounds or ground corncobs). A granular composition may also be manufactured by compressing the active substance together with powdered minerals in the presence of lubricants and binders and disintegrating and sieving the compressed product to the desired grain size. Granular compositions may be manufactured in a different manner by mixing the active substance in powder form with powdered fillers, and then glomulating the mixture with liquid to the desired particle size.

Dusting powders can be obtained by intimately mixing the active substance with an inert solid powdered carrier material, for example, talcum.

Dispersible powders are prepared by mixing 0 to 80 parts by weight of a solid inert carrier, for example, kaolin, dolomite, gypsum, chalk, bentonite, attapulgite, colloidal $SiO_2$ or mixtures of these and similar substances, with 10 to 95 parts by weight of the active substance, 1 to 5 parts by weight of a dispersing agent, for example, the lignine sulphonates or alkylnaphthalene sulphonates known for this purpose, preferably also 0.5 to 5 parts by weight of a wetting agent, for example, fatty alcohol sulphates, alkyl aryl sulphonates, naphthalene sulphonates, fatty acid condensation products or polyoxyethylene compounds, and finally other additives, if so desired.

For the preparation of miscible oils the active compound is dissolved in a suitable solvent which preferably is poorly water-miscible and one or more emulsifiers are added to this solution; these miscible oils are also termed emulsifiable concentrates. Examples of suitable solvents are xylene, toluene, petroleum distillates which are rich in aromates, for example, solvent naphtha, distilled tar oil and mixtures of these liquids. As emulsifiers may be used, for example, polyoxyethylene compounds and/or alkylaryl sulphonates. The concentration of the active compounds in the said miscible oils is not restricted to narrow limits and may vary, for example, between 2 and 50% by weight.

In addition to a miscible oil may be mentioned as a liquid and highly concentrated primary composition a solution of the active substance in a readily water-miscible liquid, for example, a glycol, a glycol ether, dimethyl formamide, or N-methyl pyrrolidone, to which solution an emulsifier and/or optionally one or more surface-active substances are added: DC. An aqueous solution or dispersion of the active substance is obtained upon diluting with water shortly before or during spraying.

An aerosol composition according to the invention is obtained in the usual manner by incorporating the active substance, optionally in a solvent, in a volatile liquid to be used as a propellant, for example, a mixture of lower hydrocarbons, dimethyl ether, or gases, for example, carbon dioxide, nitrogen or nitrous oxide.

Fumigating agents, for example, fumigating candles or fumigating powders, i.e. compositions which during burning can develop a pesticidal smoke, are obtained by taking up the active substance in a combustible mixture which may comprise as a fuel, for example, a sugar or a wood, preferably in a ground form, a substance to maintain combustion, for example, ammonium nitrate or potassium chlorate, and further a substance to delay combustion, for example, kaolin, bentonite and/or colloidal silicic acid.

In addition to the ingredients mentioned hereinbefore, the compositions according to the invention may also comprise other substances known for use in the said agents. For example, a lubricant, e.g. calcium stearate or magnesium stearate, may be added to a dispersible powder or a mixture to be granulated. "Adhesives", for example, polyvinyl alcohol, cellulose derivatives or other colloidal materials, such as casein, may also be added to improve the adhesion of the pesticide to the crop. Furthermore, a substance may be added to reduce the adhesion phytotoxicity of active substance, carrier material or auxiliary substance, for example, wool fat or wool fatty alcohol, and synergistically active substances, for example, piperonyl butoxide, may be incorporated in the composition.

Pesticidal compounds known per se may also be incorporated in the compositions according to the invention. As a result of this the activity spectrum of the composition is widened and synergism may occur.

The following insecticidal, acaricidal and fungicidal compounds known per se may be considered for use in such a combination composition.

INSECTICIDES, FOR EXAMPLES:
1. organic chlorine compounds, for example, 6,7,8,9,10,10-hexachloro-1,5,5a, 6,9,9a-hexahydro-6,9-methano-2,4,3-benzo[e]-dioxathiepine 3-oxide;
2. carbamates, for example, 2-dimethylamino-5,6-dimethyl-pyrimidin-4-yl dimethyl carbamate and 2-isopropoxyphenyl methyl carbamate;
3. di(m)ethyl phosphates, for example, 2-chloro-2-diethyl-carbamoyl-1-methyl vinyl-, 2-methoxycarbonyl-1-methyl-vinyl-, 2-chloro-1-(2,4-dichlorophenyl)vinyl-, and 2-chloro-1-(2,4,5-trichlorophenyl)vinyl di(m)ethylphosphate;
4. O,O-di(m)ethyl phosphorothioates, for example, O(S)-2-methyl-thioethyl-, S-2-ethylsulphinyl ethyl-, S-2-(1-methylcarbamoylethylthio)ethyl-, O-4-bromo-2,5-di-chlorophenyl-, O-3,5,6-trichloro-2-pyridyl-, O-2-isopropyl-6-methylpyrimidin-4-yl-, and O-4-nitrophenyl O,O--di(m)ethyl phosphorothioate;
5. O,O-di(m)ethyl phosphorodithioates, for example, S-methyl carbamoyl methyl-, S-2-ethylthioethyl-, S-(3,4-dihydro-4-oxobenzo[d]-1,2,3-triazin-3-ylmethyl)-, S-1,2-di(ethoxycarbonyl)ethyl-, S-6-chloro-2-oxobenzoxazo-lin-3-ylmethyl-, and S-2,3-dihydro-5-methoxy-2-oxo-1,3,4-thiodiazol-3-yl-methyl O,O-di(m)ethyl phosphorodithioate;
6. phosphonates, for example, dimethyl 2,2,2-trichloro-1-hydroxyethyl phosphonate;
7. benzoyl urea, for example, N-(2,6-difluorobenzoyl)-N'-(4-chlorophenyl)urea;
8. pyrethrines and pyrethroids;
9. amidines, for example, N'-(2-methyl-4-chlorophenyl)-N,N-dimethyl formamidine; and
10. microbial insecticides, for example, Bacillus thuringiensis.

ACARIDICES, FOR EXAMPLE:
1. organic tin compounds, for example, tricyclohexyl tin hydroxide and di [tri-(2-methyl-2-phenyl-propyl)tin]oxide;
2. Organic halogen compounds, for example, isopropyl 4,4'-dibromobenzilate, 2,2,2-trichloro-1,1-di(4-chlorophenyl)ethanol and 2,4,5,4'-tetrachlorodiphenyl sulphone;

and furthermore: 3-chloro-α-ethoxyimino-2,6-dimethoxybenzyl benzoate, O,O-dimethyl S-methylcarbamoylmethyl phosphorothioate and 1-[4-{N-(4-chloro-α-cyclopropylbenzylidene)-amino-oxymethyl} phenyl]-3-(2,6-difluorobenzoyl)urea.

FUNGICIDES, FOR EXAMPLES:
1. organic tin compounds, for example, triphenyl tin hydroxide and triphenyl tin acetate;
2. alkylene bisdithiocarbamates, for example, zinc ethylene bisdithiocarbamate and manganese ethylene bisdithiocarbamate;
3. 1-acyl- or 1-carbamoyl-N-benzimidazole(-2)carbamates and 1,2-bis(3-alkoxycarbonyl-2-thiureido)-benzene; and furthermore 2,4-dinitro-6-(2-acetyl-phenylcrotonate), [1-bis(dimethylamino)phosphoryl]-3-phenyl-5-amino-1,2,4-triazole, N-trichloromethylthiophthalimide, N-trichloromethyl-thiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'thiazolyl)-benzimidazole, 5-butyl-2-ethylamino-6-methyl-pyrimidine-4-yl-dimethyl sulphamate, 1-(4-chlorophenoxy)-3,3-dimethyl-1-(1,2,4-triazol-1-yl)-2-butanone, 1-[2-(2,4-dichlorophenyl)-4-propyl-1,3-dioxolan-2-ylmethyl]-1H-1,2,4-triazole, 2,4'-difluoro -α-(1H-1,2,4-triazol-1-ylmethyl-benzhydryl alcohol,α-(2-chlorophenyl)-α-(4-fluorophenyl)-5-pyrimidine methanol, α-(2-chlorophenyl)-α-(4-chlorophenyl)-5-pyrimidine methanol, 1-(isopropylcarbamoyl)-3-(3,5-dichlorophenyl)hydantoin, N-(1,1,2,2,-tetrachloroethylthio)-4-cyclohexene-1,2-carboximide, N-trichloro-methylmercapto-4-cyclohexene-1,2-dicarboximide, N-tridecyl-2,6-dimethylmorpholine, 5,6-dihydro-2-methyl-1,4-oxathiine-3-carboxanilide, 2,4,5-trimethyl-N-phenyl-3-furancarboxamide, 2,5-dimethyl-N-cyclohexyl-N-methoxy-3-furancarboxamide and N-phenyl-2-methylfuran-3-carboxamide.

Of course, the dosage of the composition according to the invention desired for practical applications will depend on various factors, for example, application area, selected active substance, form of composition, nature and extent of the infection and the weather conditions.

In general it holds that favorable results are reached with a dosage which corresponds to 10 to 5,000 g of the active substance per hectare, preferably 50 to 500 g per hectare.

The aphicidal activity can even be improved by adding one or more of the following substances to the compositions according to the invention: an aliphatic or naphthenic mineral oil, a vegetable oil, a glycol ether, an alkylated benzene, a polyoxyethylene compound, urea, a polymeric resin compound and a surface-active substance, for example, a polyoxyethylene-sorbitan ester, a fatty acid polyglycol ester, an alkylated phenol-polyoxyethylene, a polyoxyethylene alkyl ether, a quaternary ammonium compound, or a synergist, for example, piperonyl butoxide. The additives to be used must, of course, cause no or at least no noticeable phytotoxicity. The composition may also comprise a small quantity of a phytotoxicity-reducing substance, for example, wool fat, wool fatty alcohol, wool fatty acid or an ester of wool fatty alcohol or wool fatty acid. The quantity of the additive may vary within wide limits, depending on the application, and is usually between 10 and 10,000 ml per hectare.

It has been found that the compounds according to the invention also have an interesting systemic activity, i.e. after taking up by the roots of the plant, kill insects, in particular aphids, on the plant. This activity was even found upon infecting afterwards, so a few weeks after the treatment with the active substance: residual activity.

In various compounds according to the invention an interesting activity has also been established with regard to other insects, for example, larvae and adults of *Plutella xylostella, Spodoptera littoralis, Leptinotarsa decemlineata* and other beetles.

The compounds according to the invention are new substances which may be prepared in a manner known per se for the synthesis of related compounds.

For example, the new compounds according to the invention may be prepared by acylating the 5-unsubstituted barbituric acid derivative of the general formula

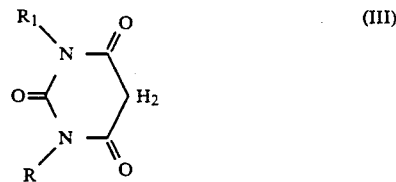

wherein R and $R_1$ have the meanings given hereinbefore, in particular with the aid of an acid anhydride, acid halide or carboxylic acid of the general formula

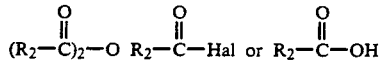

wherein $R_2$ has the meaning given hereinbefore and Hal is a halogen atom, preferably a chlorine atom. The reaction with the acid halide may be promoted by the addition of an at least equimolar quantity of an organic base, for example, an amine such as pyridine or triethylamine.

The acylation may be carried out without a solvent or in a suitable solvent. In the former case an excess of an acid anhydride or acid chloride may be used which, as it were, serves as a solvent. Suitable solvents for the reaction are inert solvents, for example, ethers or halogenated hydrocarbons. This reaction is preferably carried out at a temperature between room temperature and the boiling-point of the used acylating agent or solvent, respectively. When an organic base is used to promote the acylation reaction, the said organic base may also serve as a solvent for the reaction. When an organic base is used it is often not necessary to heat the reaction mixture to obtain the desired result. Room temperature or a temperature reduced to approximately 0° C. is then often sufficient to produce the acylation.

The barbituric acid derivative of the general formula III, unsubstituted in the 5-position and required for the above acylation reaction, may be prepared by reaction of the urea compound in question with malonic acid or a derivative hereof. Dialkyl malonate or malonyl halide may be considered as malonic acid derivatives suitable for this reaction. For example, a urea derivative of the general formula $R-NH-CO-NH-R_1$, whether or not influenced by a sodium alkoxide, may be reacted with an equimolar quantity of a dialkyl malonate, in which the desired product may be obtained after working-up. This product may also be synthetised by reaction of the above urea derivative with an equimolar quantity of malonyl chloride under the influence of an organic base or by the addition of malonic acid to a carbodiimide of the general formula $R-N=C=N-R_1$. The barbituric acid derivative may also be prepared from the above urea derivative and malonic acid, for example, in the presence of an acid anhydride such as acetic acid anhydride. The 5-unsubstituted barbituric acid derivative is preferably not isolated separately but is directly converted into the desired final product.

The invention will now be described in greater detail with reference to the ensuing specific examples.

EXAMPLE I

Preparation of 1-phenyl-3-methylallyl-5-acetyl barbituric acid (1)

a) A quantity of 33.4 g of 1-methylallyl-3-phenyl urea is stirred with 18.3 g of malonic acid in 100 ml of acetic acid anhydride at 75° C. for 4 hours. After evaporating in vacuo the residue is shaken out with water and then taken up in 2N sodiumhydroxide solution. The aqueous solution is washed with diethyl ether and then acidified with conc. hydrochloric acid and extracted with methylene chloride. After separation, the organic layer is washed with water, dried, filtered and evaporated. The desired product, namely 1-phenyl-3-methylallylbarbituric acid, is obtained in a yield of 35.5 g. The product can be purified by column chromatography by using a silica gel column and ethyl acetate as an eluent. The pure product is then obtained as a pale yellow syrupy liquid.

(b) The acetylation is carried out by refluxing the product obtained sub (a) in a quantity of 11.6 g for 8 hours in 150 ml of acetic acid anhydride. After leaving to stand overnight the reaction mixture is evaporated in vacuo. The residue is then washed with water and is then taken up in methylene chloride. The organic layer—after washing with water, drying and evaporating—yields a product which is purified by column chromatography: silica gel/methylene chloride. The main fraction is stirred with 4N hydrochloric acid, separated, washed with water, dried, and evaporated in vacuo. The desired final product, viz. 1-phenyl-3-methylallyl-5-acetyl barbituric acid (1) is obtained in a yield of 6.90 g; melting-point 104° C.

The following compounds are prepared in a corresponding manner, in which, if desired, the final product is purified by recrystallisation instead of chromatography; the numbers correspond to the numbers of the compounds used hereinbefore:

| Comp. nr. | Phys. data |
|---|---|
| 2 | m.p. 62–65° C. |
| 3 | m.p. 114–117° C. |
| 4 | MS: m/z = 320(M+) |
| 15 | m.p. 76–81° C. |
| 16 | m.p. 118–120° C. |
| 17 | MS: m/z = 320(M+) |

-continued

| Comp. nr. | Phys. data |
|---|---|
| 18 | MS: m/z = 335(M+) |

EXAMPLE II

Preparation of 1-phenyl-3-cyclopropylmethyl-5-acetyl-barbituric acid (5)

A quantity of 4.75 g of 1-cyclopropylmethyl-3-phenyl urea and 2.60 g of malonic acid are heated in 30 ml of acetic acid anhydride at 75° C. for 4 hours. After cooling slowly, the acetic acid anhydride is evaporated in vacuo. The residue is boiled in ethanol, cooled and filtered. The resulting crystalline product is the title compound (5) and melts at 91°-95° C.; yield 5.21 g.

EXAMPLE III

Preparation of 1-(4-fluorophenyl)-3-methylallyl-5-acetyl-barbituric acid (6)

1-(4-Fluorophenyl)-3-methylallyl barbituric acid is prepared as described in example Ia). A quantity of 2.81 g of this substance is dissolved in 25 ml of pyridine. 0.92 ml of acetic acid anhydride is added to this solution while stirring and cooling to 0° C. After stirring at 0° C. for 30 minutes and at room temperature for 4 hours, the pyridine is evaporated in vacuo. 50 ml of water are added to the residue, which then is acidified with conc. hydrochloric acid and extracted with methylene chloride. After separating, the organic layer is washed with water, dried and evaporated. The resulting title compound (6) is recrystallized from ethanol and then has a melting-point of 108°-109° C.; yield 1.82 g.

In a corresponding manner, in which the final product is purified optionally by chromatography or by means of cuproacetate/ethanol, the following compounds are prepared:

| Comp. nr. | Phys. data |
|---|---|
| 7 | m.p. 114-117° C. |
| 9 | MS: m/z = 311(M+) |
| 10 | MS: m/z = 309(M+) |
| 11 | MS: m/z = 318(M+) |
| 12 | MS: m/z = 330(M+) |
| 19 | MS: m/z = 327(M+) |
| 20 | MS: m/z = 378(M+) |
| 23 | m.p. 65-70° C. |
| 33 | m.p. 87-94° C. |
| 34 | m.p. 125-139° C. |
| 35 | m.p. 88-93° C. |
| 36 | m.p. 148-151° C. |
| 37 | m.p. 165-167° C. |
| 38 | m.p. >125° C. (decomp.) |
| 39 | m.p. 153-155° C. |
| 40 | m.p. 122-128° C. |
| 41 | m.p. 101-105° C. |

EXAMPLE IV

Preparation of sodium 1-phenyl-3-propargyl-5-acetyl-barbiturate (8)

A solution of 0.23 g of sodium in 25 ml of methanol is added to a suspension of 2.84 g of 1-phenyl-3-propargyl-5-acetyl barbituric acid prepared as described in Example I, in ml of methanol. The reaction mixture is left to stand overnight while stirring, after which the methanol is evaporated. The residue is stirred with diethyl ether, sucked off and dried. The title compound (8) is obtained in a yield of 2.62 g; melting-point >260° C.

EXAMPLE V

Preparation of 1-(2-cycanophenyl)-3-methylallyl-5-acetyl-barbituric acid (14)

1-(2-Cyanophenyl)-3-methylallyl urea in a quantity of 2.15 g is stirred at 70° C. for 3.5 hours with 1.04 g of malonic acid in 15 ml of acetic acid anhydride. After slowly cooling to 0° C., 0.80 ml of pyridine is added. The reaction mixture is stirred, first at approximately 0° C. for 30 minutes and then at room temperature for 3 hours. After evaporation in vacuo the residue is washed for a moment with water. The organic layer is taken up in methylene chloride, washed with water, dried and evaporated. After stirring in diethyl ether and sucking off, the title compound (14) is obtained in a yield of 1.31 g; melting-point 119°-125° C.

The following compounds are prepared in a corresponding manner in which the final product is purified, if desired, by recrystallisation or chromatography.

| Comp. nr. | Phys. data |
|---|---|
| 13 | m.p. 161-165° C. |
| 21 | m.p. 123-125° C. |
| 24 | m.p. 151-156° C. |
| 25 | MS: m/z = 343(M+) |
| 26 | m.p. 81-85° C. |
| 27 | m.p. >200° C. (decomp.) |
| 30 | m.p. 180-181° C. |
| 31 | m.p. 96-100° C. |
| 32 | m.p. 203-206° C. |

EXAMPLE VI

Preparation of 1-phenyl-3-t.butyl-5-acetyl-barbituric acid (28)

A quantity of 3.85 g of 1-t.butyl-3-phenylurea is stirred at 0° C. in 50 ml of dry diethyl ether. 1.95 ml of malonylchloride are slowly added dropwise to this solution. After the addition of a little triethylamine the reaction mixture is slowly heated to approximately 30° C. After 2 hours 50 ml of water are added. The ether layer is separated, washed with water, dried and evaporated. After recrystallisation from ethanol, 1-phenyl-3-t.butyl-barbituric acid is obtained in a yield of 0.6 g; melting-point 118°-125° C. The resulting product is acetylated as described in Example III, the title compound (28) being obtained; melting-point 145°-148° C.

EXAMPLE VII

Preparation of 1-phenyl-3-methylallyl-5-propionyl-barbituric acid (29)

A quantity of 1.29 g of 1-phenyl-3-methylallyl-barbituric acid prepared as described in Example Ia) is dissolved in 10 ml of pyridine. 0.52 ml of propionyl chloride is added dropwise to this solution which is cooled at 0° C. The reaction mixture is stirred at approximately 0° C. for 30 minutes and then at room temperature for 3 hours, and is then poured on 50 ml of ice water. After stirring with active carbon and filtering, the filtrate is acidified with conc. hydrochloric acid and extracted with methylene chloride. The organic layer is separated, washed with water, dried and evaporated. The final product is purified by means of column chromatography: silica gel/methylene chloride. The title compound is obtained in a yield of 0.65 g; melting-point 76°–80° C.

EXAMPLE VIII

Preparation of 1-phenyl-3-cyclopropylmethyl-5-carbamoylbarbituric acid (22)

To a solution of 1.4 g 1-phenyl-3-cyclopropylmethyl-barbituric acid, obtained as described in Example Ia, in 10 ml dimethylformamide, is added a solution of 0.75 g potassium cyanate in approx. 1.5 ml water. The reaction mixture is stirred at 90°–100° C. for 1.5 hrs. After cooling down to room temperature, the mixture is poured into water, filtered, acidified with 1N hydrochloric acid and sucked off. The precipitate is washed successively with water and aqueous NaCl-solution and then dissolved in diethylether. After drying the ether layer is evaporated to dryness. The residue is washed with a small amount of diethylether and yields the desired (NMR) title compound in a quantity of 140 mg. The water layer is extracted with methylenechloride; the organic phase is separated, dried and evaporated to yield an additional portion of the desired compound. The compound (22) melts at 199°–200° C.

EXAMPLE IX (a) Preparation of a solution of an active substance, viz. 1-(3-cyanophenyl)-3-methylallyl-5-acetyl-barbituric acid (7) in a water-miscible liquid (DC)

The above active substance in a quantity of 10 g is dissolved in a mixture of 10 ml of isophorone and approximately 70 ml of dimethyl formamide to which a polyoxyethylene glycol ricinyl ether has been added as an emulsifier in a quantity of 10 g.

In a corresponding manner, from the other active substances are obtained 10- or 20% formulations in N-methyl pyrrolidone, dimethyl formamide, a mixture of N-methyl pyrrolidone and isophorone, and a glycol ether, viz. propylene glycol monomethyl ether, as solvents.

(b) Preparation of a solution of the active substance in water (SL)

200 mg Of the active substance to be investigated is made up to 4 ml with water in the presence of approximately 1.5 ml of 1N sodium hydroxide solution and approximately 20 mg of an alkylphenol polyoxyethylene. This solution—optionally after pouring out in water—may be used as a spray liquid.

(c) Preparation of an emulsifiable concentrate (EC) of the active substance 10 g of the active substance to be examined are dissolved in a mixture of 15 ml of isophorone and 70 ml of xylene; 5 g of a mixture of a polyoxyethylene sorbitan ester and an alkyl benzene sulphonate are added to this solution as an emulsifier.

(d) Preparation of a dispersible powder (WP) of the active substance 25 g of the active substance to be examined are mixed with 68 g of kaolin in the presence of 2g of sodium butylnaphthanlene sulphonate and 5 g of lignin sulphonate and then ground to the desired particle size.

(e) Preparation of a suspension concentrate (SC) of the active substance

A mixture of 10 g of active substance, 2 g of lignin sulphonate and 0.8 g of a sodium alkyl sulphonate is made up with water to a total quantity of 100 ml; the ingredients or the final product are ground, if so desired.

(f) Preparation of a granule of the active substance 7.5 g of active substance, 5 g of sulphite lye and 87.5 g of ground dolomite are mixed, after which the resulting mixture is processed to a granular composition by means of the so-called compacting method.

EXAMPLE X

ACTIVITY AGAINST *APHIS FABAE* (BLACK BEAN APHID); LABORATORY TESTS

The compounds to be tested are processed to compositions as described in Example IX (a). The following known compounds are also tested for comparison.

(a) = 1,3-dimethyl-5-acetyl-2-thiobarbituric acid,
(b) = 1,3-dimethyl-5-benzoyl-2-thiobarbituric acid;
(c) = 1,3-dimethyl-5-cyclohexylcarbonyl-2-thiobarbituric acid,
(d) = 1-methyl-3-n-propyl-5-acetyl-barbituric acid.

Young broad bean plants, approximately 10 cm high, are headed to two leaf pairs and are then sprayed with the above-mentioned compositions in various concentrations. After drying the plants are infected with *Phis fabae* (black bean aphid) by placing 10 adult aphids on each plant. The plants are then stored in a climate cell at a temperature of 21 ±1° C., a light/dark cycle of 18/6 hours being maintained with a relative humidity of approximately 65%. The mortality of the aphids is established after 7 days. Each test is carried out in quadruplicate.

The LC 90 value, i.e. the concentration of active substance at which 90% of the aphids is killed, is determined from the results obtained. This concentration is indicated in mg of active substance per liter (a.i./1).

The tested compounds according to the invention having the numbers 1, 2, 3, 4, 5, 6, 7, 8, 9, 10, 11, 12, 13, 14, 15, 16, 17, 18, 19, 20, 21, 23, 25, 26, 30, 31, 32, 36, 37, 38, 39 and 40 all have an LC90 smaller than 10 mg a.i./1. On the other hand the LC90 of the known substances a, b and c proves to be larger than 300 mg a.i./1, that of substance d proves to be between 10 and 30 mg a.i./1.

EXAMPLE XI

ACTIVITY AGAINST *APHIS FABAE*; LABORATORY TESTS

Compounds according to the invention having the numbers 1, 5, 6, 7, 8, 9, 11, 13, 19, 21, 31, 36 and 40 are processed to compositions in the same manner as in Example X and tested on *Aphis fabae* in lower concentrations. The tested compounds prove to be active in concentrations of 1 mg a.i./1 or lower and have an LC90 smaller than 1 mg a.i./1.

We claim:
1. A barbituric acid compound of the formula

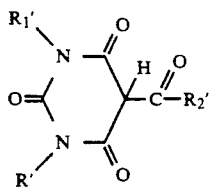 (II)

wherein
R' is an unsubstituted phenyl group or a phenyl group which is substituted with 1 or 2 substituents selected from the group consisting of halogen, nitro, cyano and $C_1$–$C_4$ alkyl,
$R'_1$ is an allyl group, a methylallyl group, a propargyl group, a cyclopropyl group or a cyclopropylmethyl group, and
$R'_2$ is a methyl group or an ethyl group,
or an alkali metal or tetra-alkyl ammonium slat, or a nickel, copper or zinc complex of the said compound.

2. A barbituric acid as defined in claim 1, which is compound (5), namely, 1-phenyl-3-cyclopropylmethyl-5-acetylbarbituric acid.

3. A barbituric acid as defined in claim 1, which is compound (13), namely, 1-(3-cyanophenyl)-3-cyclopropylmethyl-5-acetylbarbituric acid.

4. An insecticidal composition comprising in addition to a solid or liquid inert carrier material a barbituric acid compound as an active ingredient, characterized in that the active ingredient is a compound of formula (II) as shown in claim 1, wherein R', $R'_1$ and $R'_2$ have the meanings given in claim 1.

5. An insecticidal composition as defined in claim 4, wherein the barbituric acid is compound (5), namely, 1-phenyl-3-cyclopropyl-methyl-5-acetylbarbituric acid.

6. An insecticidal composition as defined in claim 4, wherein the barbituric acid is compound (13), namely, 1-(3-cyanophenyl)-3-cyclopropylmethyl-5-acetylbarbituric acid.

7. A method of controlling insects in agriculture, horticulture and silviculture, characterized in that the infected crop is treated with a composition as claimed in claim 4 in a dosage from 10 to 5,000 g of active substance per hectare.

8. A method of controlling insects as defined in claim 7, wherein the active ingredient of the insecticidal composition is compound (5), namely, 1-phenyl-3-cyclopropylmethyl-5-acetylbarbituric acid.

9. A method of controlling insects as defined in claim 7, wherein the active ingredient of the insecticidal composition is compound (13), namely, 1-(3-cyanophenyl)-3-cyclopropylmethyl-5-acetylbarbituric acid.

10. A method as defined in claim 7 wherein the insects are aphids.

11. A method as defined in claim 7 wherein the active substance is present in an amount from 50 to 500 g per hectare.

* * * * *